United States Patent [19]

Bastron

[11] Patent Number: 5,563,288
[45] Date of Patent: Oct. 8, 1996

[54] PROCESS FOR THE PREPARATION OF TERTIARY AMINOCARBONATES AND AMINOETHERS

[75] Inventor: Victor C. Bastron, Charleston, W. Va.

[73] Assignee: OSi Specialties, Inc., Tarrytown, N.Y.

[21] Appl. No.: 477,322

[22] Filed: Jun. 7, 1995

[51] Int. Cl.$^6$ .......................... C07C 68/06; C07C 209/00
[52] U.S. Cl. ............................. 558/276; 564/468
[58] Field of Search ................................. 558/276

[56] References Cited

U.S. PATENT DOCUMENTS

| | | | |
|---|---|---|---|
| 2,691,017 | 10/1954 | Dornfeld | 260/247.2 |
| 4,318,862 | 3/1982 | Romano et al. | 260/463 |
| 4,324,739 | 4/1982 | Zondler et al. | 260/465.4 |
| 4,691,041 | 9/1987 | Duranleau et al. | 558/277 |
| 4,734,518 | 3/1988 | Knifton | 558/277 |
| 5,175,333 | 12/1992 | Kerschner et al. | 558/276 X |
| 5,214,142 | 5/1993 | King | 544/111 |

FOREIGN PATENT DOCUMENTS

| | | |
|---|---|---|
| 0425197B1 | 5/1991 | European Pat. Off. . |
| 0425197A2 | 5/1991 | European Pat. Off. . |
| 0425197A3 | 5/1991 | European Pat. Off. . |
| 4203908A1 | 8/1993 | Germany . |

OTHER PUBLICATIONS

Abstract, Knifton, John F., U.S. Patent 4,734,518 A, 29 Mar. 1988.
Abstract, Duranleau, Roger G., Texaco, Inc., U.S. 4,691,041 A, 1 Sep. 1987.
F. G. Willeboordse, et al., "Kinetics and Catalysis of Urethane Foam Reactions", Journal of Cellular Plastics pp. 76–84, Jan. 1965.
Procut literature, EniChem Synthesis SpA, "Dimethyl Carbonate DMC", 1993.

*Primary Examiner*—Johann Richter
*Assistant Examiner*—Michael G. Ambrose
*Attorney, Agent, or Firm*—Cushman Darby & Cushman, L.L.P.

[57] ABSTRACT

The invention relates to processes for producing di-(tertiary aminoalkyl) carbonate including the step of reacting a tertiary alkanolamine with methyl alkyl carbonate in the presence of a transesterification catalyst to form tertiary aminoalkyl alkyl carbonate, wherein some of the tertiary alkanolamine reacts with the tertiary aminoalkyl alkyl carbonate to form di-(tertiary aminoalkyl) carbonate. The invention also relates to processes for producing di-(tertiary aminoalkyl) carbonate including the steps of (i) reacting dimethyl carbonate with an alcohol in the presence of a transesterification catalyst to form a methyl alkyl carbonate, and (ii) reacting a tertiary alkanolamine with the methyl alkyl carbonate formed in step i) in the presence of a transesterification catalyst to form tertiary aminoalkyl alkyl carbonate, wherein some of the tertiary alkanolamine reacts with the tertiary aminoalkyl alkyl carbonate to form di-(tertiary aminoalkyl) carbonate.

44 Claims, 2 Drawing Sheets

PROCESS FOR THE PREPARATION OF TERTIARY AMINOCARBONATES AND AMINOETHERS

FIELD OF THE INVENTION

The invention relates to a batch process for preparing tertiary aminocarbonates, such as bis[2-(N,N-dimethylamino)alkyl]carbonates. The tertiary aminocarbonates are desirable as intermediates in making medicinal agents, as amine curing agents for polyepoxide compounds, as catalysts for the production of polyurethane and polyurea with reduced odor, and as intermediates in making tertiary aminoethers which themselves are useful as catalysts in the production of polyurethanes, especially cellular polyurethanes.

BACKGROUND OF THE INVENTION

It is conventional and routinely accepted in the art that the easiest route for producing tertiary aminocarbonates is to transesterify diethyl carbonate (DEC) with the appropriate alkanolamine in the presence of wide variety of basic catalysts. This route involves straightforward processing and provides reasonably good yields (i.e., >80%). The route suffers from the high price of DEC, the limited sources of DEC, uncertainties about the future availability of DEC, and the burden of certain government regulations associated with handling the by-product ethanol.

In particular, DEC is manufactured almost exclusively by reacting ethanol with phosgene using technology developed over 50 years ago. Phosgene is an extremely toxic and corrosive chemical requiring great care in preventing releases. While the by-products from the phosgene-based manufacture of diethyl carbonate are not as toxic as phosgene, they are nevertheless hazardous requiring potentially troublesome disposal. Because of these environmental issues there are pressures to curtail the use of phosgene in the manufacture of intermediates. Most phosgene manufacturers are currently cautious about building new facilities especially for specialty uses such as diethyl carbonate. Since the use of DEC in making tertiary aminocarbonates requires the handling of ethanol first as a raw material in the manufacture of the DEC and then as a by-product from the tertiary aminocarbonate process, there are additional costs associated with the government requirements associated with handling ethanol.

The preparation of bis[(N,N-dialklyamino)alkyl]carbonates by transesterifying diethyl carbonate with tertiary alkanolamines in the presence of anhydrous potassium carbonate catalyst is known from U.S. Pat. No. 2,691,017. The bis[(N,N-dialklyamino)alkyl]carbonates thus produced were further reacted with various inorganic and strong organic acids to form salts which are non-toxic in therapeutic dosage. The yields of the tertiary aminocarbonates were not disclosed.

The use of bis(2-dimethylamino-ethyl)carbonate (DDC) as a catalyst for both the alcohol-isocyanate reaction and the water-isocyanate reaction in the formation of polyurethane foam is discussed in Willeboordse et al., *J. Cellular Plastics* 1(1) 76–84 (Jan, 1965). However, details of the preparation are not disclosed.

Patent application DE 4203908-A1 describes diaminocarbonate compounds of the formula R1—OC(=O)—OR2 where R1 and R2 are tertiary amino groups with methyl or $C_{2-20}$ alkyl, phenyl, or $C_{1-20}$ alkyl substituted phenyl substituents for use as catalysts in the production of polyurethane and polyurea having reduced odor. In one example, DDC was prepared by reacting 1.26 g-mole of dimethyl carbonate with 2.52 g-mole of dimethylethanolamine in the presence of potassium hydroxide catalyst. The by-product methanol was removed from the reaction mixture by azeotropic distillation with cyclohexane. The yield of DDC was 35%.

U.S. Pat. No. 4,324,739 indicates that (dimethylaminoalkyl)carboxylic acid esters are especially suitable for use as amine curing agents for polyepoxide compounds because they impart longer curing times which results in good processing properties, especially when the mixtures are used as adhesives. In one example, DDC was prepared by reacting 1 g-mole of diethyl carbonate with 2 g-mole of dimethylethanolamine using potassium hydroxide as the catalyst by distilling the by-product ethanol overhead through an 80 cm packed distillation column. The amount of DDC obtained indicates a DDC yield of 22% based on the starting DEC.

U.S. Pat. No. 5,214,142 describes a process for preparing aminoethers by decarboxylating the corresponding aminocarbonates using a suitable metal oxide catalyst at elevated temperatures. A number of examples in this patent are concerned with the decarboxylation of DDC to form bis(2-dimethylaminoethyl)ether, a commercially available polyurethane catalyst highly valued for its selectivity in catalyzing the water-isocyanate "blow" reaction. The patent describes the preparation of DDC by reacting 1 mole of diethyl carbonate with 6 moles of dimethylethanolamine (three times the stoichiometric requirement) using sodio 2-dimethylaminoethoxide as the catalyst in a reaction flask outfitted with a distillation column suitable for removing the ethanol by-product while retaining the diethyl carbonate in the kettle. The patent indicates DDC was isolated at a purity of 98.2% and a yield of 73.8% based on the starting diethyl carbonate. Dimethyl carbonate was also used as a starting material, but the resulting yields of aminoether were poor.

It has been discovered that dimethyl carbonate (DMC) can be used to manufacture tertiary aminocarbonates by partially transesterifying the DMC with a suitable alcohol (ROH) to form an intermediate carbonate MeOC(O)OR. This intermediate carbonate can then be used in a transesterification (TE) with the appropriate tertiary alkanolamine to form the desired tertiary aminocarbonate. By judicious use of processing aids (such as cyclohexane for breaking the methanol/DMC azeotrope) and recycling of the ROH the tertiary aminocarbonate yields achieved are comparable to those obtained when DEC is used.

The use of (DMC) rather than DEC for manufacturing these tertiary aminocarbonates is desirable because of DMC's greater supply options. DMC is manufactured not only from phosgene, but can also be manufactured by (1) liquid-phase oxidative carboxylation technology (U.S. Pat. No. 4,318,862) as currently practiced by EniChem Synthesis, (2) vapor-phase oxidative carboxylation technology (European Pat. No. 425,197) as currently practiced by Ube Industries, and (3) cosynthesis with ethylene glycol by reacting methanol and ethylene carbonate in the presence of either a heterogeneous catalyst (U.S. Pat. No. 4,691,041) or a homogeneous catalyst (U.S. Pat. No. 4,734,518). These technologies are either not appropriate for making DEC or the practitioners of the technologies have not seen the incentive for building facilities suitable for making DEC.

Although the oxidative carboxylation routes employ toxic carbon monoxide as a reactant, the hazards of these processes are significantly lower than those associated with phosgene. Because of the increased competition in the marketplace the price of a mole of DMC has recently been about half that of a mole of DEC for purchases in excess of 100 tons per year. Unfortunately DMC reacts with tertiary amines to give the corresponding quaternary ammonium salt with methyl carbonate as anion (EniChem Synthesis SpA, Dimethyl Carbonate Product Bulletin p. 9, 1992). In the case of DMEA these materials decompose to form undesirable by-products when the transesterification is attempted in batch equipment and the yield to DDC is typically less than 50%. DEC also incurs a transportation penalty relative to DMC since one mole of DEC weighs 31% more than one mole of DMC.

Thus, for economic reasons it is desirable that tertiary aminocarbonates (such as bis[2-dimethylaminoethyl)carbonate) be manufactured from the appropriate alkanolamine through a transesterification with dimethyl carbonate (DMC). However, because of the by-product reactions, tertiary aminocarbonates have most successfully been prepared by the transesterification of diethyl carbonate (DEC) with the alkanolamine. DEC works well, but currently costs about twice as much per mole as DMC.

However, it has been discovered that DMC can be used to manufacture tertiary aminocarbonates in batch equipment by partially transesterifying the DMC with a suitable alcohol (ROH) in the presence of a suitable catalyst to form an intermediate carbonate MeOC(O)OR. This intermediate carbonate can then be used in a transesterification with the appropriate alkanolamine in the presence of a suitable catalyst to form the desired tertiary aminocarbonate. By judicious use of processing aids (such as cyclohexane for breaking the methanol/DMC azeotrope) and recycling of the ROH the tertiary aminocarbonate yields achieved are comparable to those obtained when DEC is used.

SUMMARY OF THE INVENTION

It is therefore an object of the invention to provide methods and processes for the manufacture of carboxylated aminoethers such as tertiary aminocarbonates using dimethyl carbonate as a starting material rather than diethyl carbonate. By this invention, carboxylated aminoethers are manufactured in yields sufficiently high that dimethyl carbonate may be used as the starting material rather than diethyl carbonate. For instance, the subject process is capable of converting DMC to di-tertiary aminocarbonates in yields of about 90% with purities greater than 99% using readily available chemical processing equipment.

The use of dimethyl carbonate is especially preferable not only because the cost of the dimethyl carbonate is typically lower than the cost of the diethyl carbonate, but the cost of all of the raw materials and consumed processing aids used in the process can be equivalent or lower, despite the inefficiencies associated with DMC forming quaternary ammonium salts whereby the alkanolamine as well as the DMC is consumed. Thus, another benefit of the process is that it enables the manufacture of aminocarbonates at a lower price using a readily available raw material. In addition, this invention is especially suitable for use in equipment operated in a batch mode.

For instance, one embodiment of the invention relates to a two-step process for producing di-(tertiary aminoalkyl) carbonate comprising the steps of:

i) reacting dimethyl carbonate with an alcohol in the presence of a transesterification catalyst to form a methyl alkyl carbonate and methanol, and ii) reacting a tertiary alkanolamine with the methyl alkyl carbonate formed in step i) in the presence of a transesterification catalyst to form tertiary aminoalkyl alkyl carbonate and methanol, wherein some of the tertiary alkanolamine reacts with the tertiary aminoalkyl alkyl carbonate to form di-(tertiary aminoalkyl) carbonate and alkyl alcohol, under conditions such that the methanol and alkyl alcohol are removed continuously by distillation so that the reactions of steps i) and ii) proceed toward formation of di-(tertiary aminoalkyl) carbonate.

Preferably, step i) of the above process occurs under such conditions that some of the methyl alkyl carbonate reacts with the alcohol to form di-alkyl carbonate. Consequently, preferably step ii) of the above process occurs under such conditions that some of the tertiary alkanolamine also reacts with the di-alkyl carbonate formed in step i) to form more tertiary aminoalkyl alkyl carbonate.

It is another object of the invention to provide methods and processes for the manufacture of carboxylated aminoethers including tertiary aminocarbonates in sufficiently high yields, where methyl alkyl carbonate is used as the starting material. For instance, one embodiment of the invention relates to a one-step process for producing di-(tertiary aminoalkyl) carbonate comprising the step of reacting a tertiary alkanolamine with methyl alkyl carbonate in the presence of a transesterification catalyst to form tertiary aminoalkyl alkyl carbonate and methanol, wherein some of the tertiary alkanolamine reacts with the tertiary aminoalkyl alkyl carbonate to form di-(tertiary aminoalkyl) carbonate and alkyl alcohol, under conditions such that the methanol and alkyl alcohol are removed on a continuing basis by distillation so that the reactions proceed toward formation of di-(tertiary aminoalkyl) carbonate.

In a preferred embodiment, the invention relates to a two-step process for producing bis[2-(N,N-dimethylamino)ethyl]carbonate comprising the steps of:

i) reacting dimethyl carbonate with isopropanol in the presence of a transesterification catalyst and an azeotroping agent to form methyl isopropyl carbonate and methanol, under such conditions that the methyl isopropyl carbonate reacts with the isopropanol to form di-isopropyl carbonate, ii) reacting 2-(N,N-dimethylamino)ethanol with the methyl isopropyl carbonate formed in step i) in the presence of a transesterification catalyst to form isopropyl 2-dimethylaminoethyl carbonate and methanol, under such conditions that the 2-(N,N-dimethylamino)ethanol also reacts with the di-isopropyl carbonate formed in step i) to form more isopropyl 2-dimethylaminoethyl carbonate, wherein the 2-(N,N-dimethylamino)ethanol reacts with the isopropyl 2-dimethylaminoethyl carbonate formed in step ii) to form bis[2-(N,N-dimethylamino)ethyl] carbonate and isopropanol, under conditions such that the methanol and isopropanol are removed continuously by distillation so that the reactions of steps i) and ii) proceed toward formation of bis[2-(N,N-dimethylamino)ethyl] carbonate.

In another preferred embodiment, the invention relates to a one-step process for producing bis[2-(N,N-dimethylamino)ethyl]carbonate comprising the step of reacting 2-(N,N-dimethylamino)ethanol with methyl isopropyl carbonate in the presence of a transesterification catalyst to form isopropyl 2-dimethylaminoethyl carbonate and methanol, wherein the 2-(N,N-dimethylamino)ethanol reacts with the isopropyl 2-dimethylaminoethyl carbonate to form bis[2-(N,N-dimethylamino)ethyl] carbonate and isopropanol, under conditions such that the methanol and isopropanol are removed continuously by distillation so that the reactions proceed toward formation of bis[2-(N,N-dimethylamino)ethyl] carbonate.

It is also an object of the invention to provide methods and processes for the manufacture of aminoethers including bis[2-(N,N-dialkylamino)alkyl]ethers (BDEE). In one embodiment of the invention bis[2-(N,N-dimethylamino)ethyl]ether is produced by a process comprising the steps of:

i) producing bis[2-(N,N-dimethylamino)ethyl]carbonate by one of the above-described methods; and ii) contacting the bis[2-N,N-dimethylamino)ethyl]carbonate produced in step i) with a metal oxide catalyst under conditions effective to produce the bis[2-(N,N-dimethylamino)ethyl]ether.

The above-described processes for the manufacture of aminoethers may further include a process for refining the aminoethers produced thereby. More specifically, the process for refining comprises the step of refining the aminoethers by vacuum distillation.

It is also an object of the invention to provide methods and processes for the manufacture of tetramethylethylenediamine (TMEDA). In one embodiment, the invention relates to a process for producing tetramethylethylenediamine comprising the steps of:

i) producing bis[2-(N,N-dimethylamino)ethyl]carbonate by one of the above-described processes; and ii) contacting the bis[2-N,N-dimethylamino)ethyl]carbonate produced in step i) with a metal oxide catalyst under conditions effective to produce the tetramethylethylenediamine.

Additional objects and embodiments of the invention will become apparent from the further description of the invention below.

DETAILED DESCRIPTION OF THE INVENTION

Figure 1:
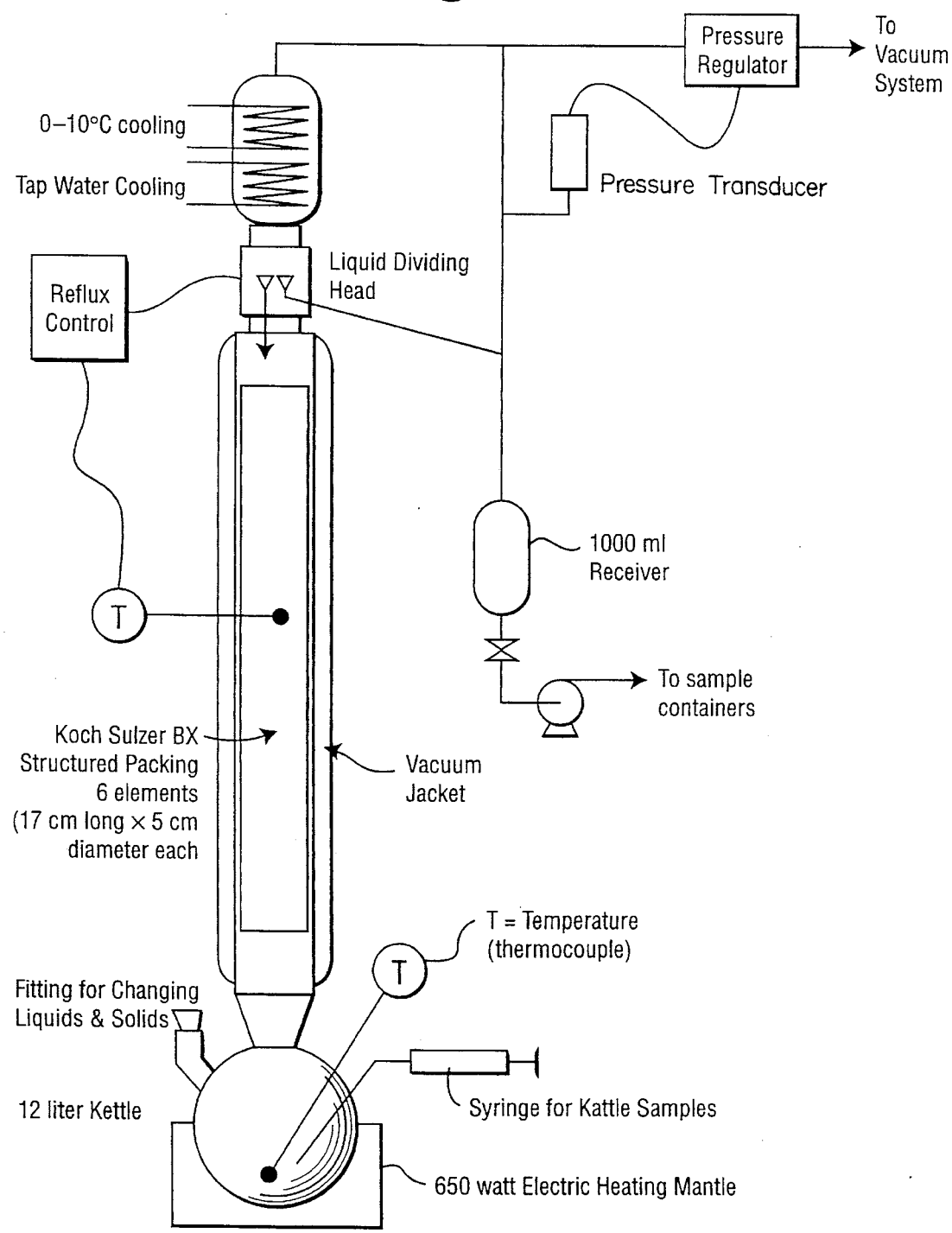
FIG. 1 is an experimental distillation apparatus.

For purposes of this invention, the following abbreviations and definitions apply:
BDEE—bis[2-(N,N-dimethylamino)ethyl]ether
DDC—bis[2-(N,N-dimethylamino)ethyl]carbonate
DEC—diethyl carbonate
DiiPC—diiso-propyl carbonate
DinPC—di-n-popropyl carbonate
DiR$_e$C—dialkyl carbonate
DMC—dimethyl carbonate
DMEA—2-(N,N-dimethylamino)ethanol=dimethylethanolamine
DMEAiPC—[2-(N,N-dimethylamino)ethyl]iso-propyl carbonate
EDC—ethyl [2-(N,N-dimethylamino)ethyl]carbonate
GC—gas chromatograph or gas chromatographic
gm—gram
K2CO3—potassium carbonate
MDC—methyl [2-(N,N-dimethylamino)ethyl]carbonate
MiPC—methyl iso-propyl carbonate
MR$_e$C—methyl alkyl carbonate
Reflux Ratio—(ml/min of overhead returned to column)/(ml/min of overhead taken as make)
R$_e$OH—an alcohol suitable for transesterifying DMC
ROH—an alcohol
TMEDA—tetramethylethylenediamine yield—(moles of usable product/maximum theoretical moles of product)×100%
%—percent by weight except for yields which are molar The processes of the invention involve both one-step and two-step transesterifications for the production of carboxylated aminoethers.

The two-step process entails partially transesterifying dimethyl carbonate with a suitable alcohol in the presence of a suitable catalyst yielding a mixed methylalkyl carbonate which is subsequently transesterified with the appropriate tertiary alkanolamine to yield the desired tertiary aminocarbonate.

For instance, one embodiment of the two-step process for producing di-(tertiary aminoalkyl)carbonate comprises the steps of:

i) reacting dimethyl carbonate with an alcohol in the presence of a transesterification catalyst to form a methyl alkyl carbonate and methanol, and ii) reacting a tertiary alkanolamine with the methyl alkyl carbonate formed in step i) in the presence of an effective amount of a transesterification catalyst to form tertiary aminoalkyl alkyl carbonate and methanol, wherein some of the tertiary alkanolamine reacts with the tertiary aminoalkyl alkyl carbonate to form di(tertiary aminoalkyl) carbonate and alkyl alcohol. The process of steps i) and ii) takes place under conditions such that the methanol and alkyl alcohol are removed continuously by distillation so that the reactions of steps i) and ii) proceed toward formation of di-(tertiary aminoalkyl) carbonate.

The equilibrium constants for these reactions shown in the table below are comparable to the constants of other transesterification reactions. Further, as persons skilled in this art would know, transesterification reactions are driven by, for instance, removing a by-product alcohol to counteract for the reverse reactions.

| Equilibrium Constants For Transesterification Reactions | | | | | |
|---|---|---|---|---|---|
| R | R' | Temp °C. | Solvent | K$_1$ | K$_2$ |
| Et— | Me$_2$NCH$_2$CH$_2$— | ca 85 | DMEA | 0.8 | 0.2 |
| Me— | iPr— | ca 103 | cyclohexane | 1.0 | 0.35 |
| iPr— | Me$_2$NCH$_2$CH$_2$— | ca 85 | DMEA | 0.8 | 0.3 | where

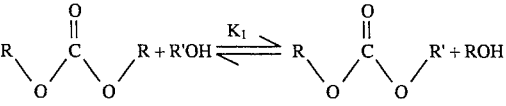

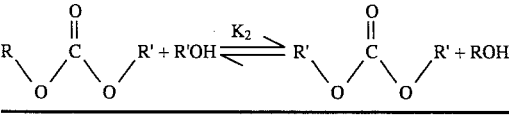

Preferably, the starting materials are essentially dry, that is, contains no more than 0.1 weight percent water and preferably no more than 0.050 weight percent water. The presence of water is disadvantageous in this reaction because it inhibits or destroys the catalyst. However, even if more than 0.1 weight percent water is present in the reaction mixture, the amount of the transesterification catalyst in step i) can be appropriately increased to counterbalance the water.

Preferably, step i) of the above process occurs under such conditions that some of the methyl alkyl carbonate reacts with the alcohol to form di-alkyl carbonate. Consequently, preferably step ii) of the above process occurs under such conditions that some of the tertiary alkanolamine also reacts with the di-alkyl carbonate formed in step i) to form more tertiary aminoalkyl alkyl carbonate.

For step i), the alcohol should have a boiling point at least 5° C. below the boiling point of the tertiary alkanolamine, and 5° C. higher than the boiling point of methanol, which is 64.7° C. at 1 atm. Preferably, the alcohol has a boiling point at least 10° C. below the boiling point of the tertiary alkanolamine. Step i) runs best with an excess of alcohol. Examples of preferred alcohols are selected from the group consisting of ethanol, i-propanol, n-propanol, n-butanol, sec-butanol, tert-butanol and isomers of amyl alcohol. Most preferred among these alcohols are i-propanol, n-propanol, n-butanol and sec-butanol.

The transesterification catalyst of step i) is selected from the group consisting of sodium alkoxides, potassium alkoxides, lithium alkoxides, cesium alkoxides and potassium carbonate. Preferably, the catalyst is one of potassium carbonate, sodium methoxide or potassium methoxide. However, as someone skilled in the art would appreciate, other catalysts known in the art may be employed for the purposes of the invention.

It is preferred that the reaction of step i) occurs in the presence of an effective amount of an azeotroping agent. The azeotroping agent is preferably selected from the group consisting of benzene, carbon tetrachloride, chloroform, cyclohexane, n-heptane, mixed isomers of heptane, n-hexane, mixed isomers of hexane, toluene and trichloroethylene. Most preferable is cyclohexane.

In a preferred embodiment of the two-step process bis[2-(N,N-dimethylamino)ethyl]carbonate is produced by a process which comprises the steps of:

i) reacting dimethyl carbonate with isopropanol in the presence of an effective amount of a transesterification catalyst and an effective amount of an azeotroping agent to form a methyl isopropyl carbonate and methanol, under such conditions that the methyl isopropyl carbonate reacts with the isopropanol to form di-isopropyl carbonate, ii) reacting 2-(N,N-dimethylamino)ethanol with the methyl isopropyl carbonate formed in step i) in the presence of a transesterification catalyst to form isopropyl 2-dimethylaminoethyl carbonate and methanol, under such conditions that the 2-(N,N-dimethylamino)ethanol also reacts with the diisopropyl carbonate formed in step i) to form more isopropyl 2-dimethylaminoethyl carbonate, wherein the 2-(N,N-dimethylamino)ethanol reacts with the isopropyl 2-dimethylaminoethyl carbonate formed in step ii) to form bis[2-(N,N-dimethylamino)ethyl] carbonate and isopropanol, under conditions such that the methanol and isopropanol are removed continuously by distillation so that the reactions of steps i) and ii) proceed toward formation of bis[2-(N,N-dimethylamino)ethyl] carbonate.

In this preferred embodiment, the transesterification catalyst in step i) is preferably sodium methoxide or potassium carbonate, the transesterification catalyst in step ii) is preferably potassium carbonate, and the azeotroping agent is preferably cyclohexane. For batch operations, the recommended grade of potassium carbonate is Armand Products' Potassium Carbonate Extra Fine.

The overall transesterification can be carried out as a reactive batch distillation in which all of the reactions occur in the kettle. Stripping methanol and isopropanol overhead is important to drive the respective reactions toward completion. Based on laboratory experiments, reaction times of 3 to 15 hours for each of the TE exchanges produce DDC yields of about 85%. This allows a reasonably wide range of adjustable column design parameters including reflux ratio, reboiler/condenser duties, etc. to keep the times for each TE exchange at less than 15 hours.

The important thing to understand about both of the TE exchanges is that the reactions and the separations are closely coupled: the distillations cannot be done if the reactions do not occur and the desired reactions will not proceed efficiently if the by-product alcohols are not removed at a rapid enough rate. Since a number of azeotropes can be involved, the TE exchanges are further complicated in that the wrong components will come overhead if the TE reactions fail to run properly. To maximize efficiency, it should be kept in mind that if either the reactions or the separations fail to proceed at the proper pace the entire operation will take too long and unacceptable levels of by-products will be formed.

Step i) is carried out at atmospheric or super atmospheric pressure and is temperature constrained overhead by the condenser cooling water temperature required to condense cyclohexane-methanol (bp=54° C.) and in the kettle by decomposition concerns at elevated temperatures (>ca 150° C.). Reaction kinetics are fast enough so that the batch cycle time will depend on the physical constraints of the system; i.e., reboiler/condenser duty, column size and pressure drop, etc.

The methanol produced in the first reaction forms a binary azeotrope with DMC (containing about 30% wt DMC) which boils at 63.8° C. The effect of cyclohexane addition is twofold: (1) it suppresses the methanol-DMC azeotrope thereby reducing DMC losses overhead and (2) it facilitates methanol removal by forming a low boiling cyclohexane-methanol azeotrope (54° C.). DMC loss overhead is reduced to about 2 wt% of the distillate.

Generally, reflux ratio does not affect the overall conversion of DMC to DDC since azeotropic compositions are involved and no further separation is accomplished at higher reflux. Laboratory studies have shown, however, that higher reflux ratios (10:1 vs. 3:1) do further reduce the amount of DMC loss to less than 1% but the increased batch time and energy penalty virtually offset potential variable cost savings.

During step ii), the kettle temperature and overall reaction time should be minimized to reduce impurities generated in the kettle. This is achieved by removing the isopropanol at reduced pressures (400 to 100 mmHg) to maintain a kettle temperature below 95° C. and by using lower reflux ratios to reduce the time-at-temperature.

With relatively dry raw materials (<0.1 wt % water) the process reactions do not appear to be mass transfer or kinetically limited, but instead, equilibrium limited and are controlled by the rate of methanol removal in the first reaction; isopropanol in the second. This is constrained by the heat removal rate in the condenser, which is dependent on the condenser coolant temperature and required condensation temperatures.

In a further embodiment, the invention entails a one-step process for producing di-(tertiary aminoalkyl) carbonate. The process comprises the step of reacting a tertiary alkanolamine with methyl alkyl carbonate in the presence of a transesterification catalyst to form tertiary aminoalkyl alkyl carbonate and methanol, wherein some of the tertiary alkanolamine reacts with the tertiary aminoalkyl alkyl carbonate to form di-(tertiary aminoalkyl) carbonate and alkyl alcohol, under conditions such that the methanol and alkyl alcohol are removed on a continuing basis by distillation so that the reactions proceed toward formation of di-(tertiary aminoalkyl) carbonate.

The methyl alkyl carbonate can be selected from the group consisting of methyl isopropyl carbonate, methyl n-propyl carbonate, methyl ethyl carbonate, methyl n-butyl carbonate, methyl sec-butyl carbonate, methyl tert-butyl carbonate, and mixed isomers of methyl amyl carbonate. Preferably, the methyl alkyl carbonate is one of methyl isopropyl carbonate, methyl n-propyl carbonate, methyl n-butyl carbonate and methyl sec-butyl carbonate.

Under certain circumstances, it is preferred that the reaction of a tertiary alkanolamine with methyl alkyl carbonate in the presence of a transesterification catalyst occurs in the presence of an azeotroping agent. The azeotroping agent is preferably selected from the group consisting of benzene, carbon tetrachloride, chloroform, cyclohexane, n-heptane, mixed isomers of heptane, n-hexane, mixed isomers of hexane, toluene and trichloroethylene. Most preferred is cyclohexane. Azeotropes are useful in the invention to keep the kettle temperature low and to minimize by-products.

Examples of tertiary alkanolamine contemplated by the processes of this invention include 2-(N,N-dimethylamino)ethanol, 2-(N,N-dimethylamino)-1-methylethanol, 3-(N,N-dimethylamino)propanol, 2-(N,N-diethylamino)ethanol and 4-(2-hydroxyethyl)morpholine. This list is not limiting and, as someone skilled in the art would recognize, the choice of tertiary alkanolamine depends upon the desired product di-tertiary aminoalkyl carbonate.

Preferably, the transesterification catalyst in the reaction of a tertiary alkanolamine with methyl alkyl carbonate is selected from the group consisting of sodium alkoxides, potassium alkoxides, lithium alkoxides, cesium alkoxides and potassium carbonate. Most preferred from this list is potassium carbonate.

Preferably, the di-tertiary aminoalkyl carbonate in the above-described processes is selected from the group consisting of bis[2-(N,N-dimethylamino)ethyl]carbonate, bis[2-(N,N-dimethylamino)-1-methylethyl]carbonate, bis[3-N,N-dimethylamino)propyl]carbonate, bis[2-(N,N-diethylamino)ethyl]carbonate and bis(2-N-morpholinoethyl)carbonate.

In a preferred embodiment of the one-step process, bis[2-(N,N-dimethylamino)ethyl]carbonate is produced by the process comprising the step of reacting 2-(N,N-dimethylamino)ethanol with methyl isopropyl carbonate in the presence of a transesterification catalyst to form isopropyl 2-dimethylaminoethyl carbonate and methanol, wherein the 2-(N,N-dimethylamino)ethanol reacts with the isopropyl 2-dimethylaminoethyl carbonate to form bis[2-(N,N-dimethylamino)ethyl] carbonate and isopropanol, under conditions such that the methanol and isopropanol are removed continuously by distillation so that the reactions proceed toward formation of bis[2-(N,N-dimethylamino)ethyl] carbonate.

In this preferred embodiment, the transesterification catalyst is preferably potassium carbonate.

The invention also contemplates methods and processes for the manufacture of aminoethers, such as bis[2-(N,N-dialkylamino)alkyl]ethers. The processes of this invention are useful for preparing substituted and unsubstituted aminoethers such as those embraced by the formulae $ROR_4$ or $ROR_5$, wherein R is the residue of an organic compound containing nitrogen, $R_4$ is hydrogen, halogen, amino, hydroxyl or the residue of an organic compound, and $R_5$ is amino, hydroxyl or the residue of an organic compound. The R and $R_4$ substituents together and the R and $R_5$ substituents together can complete a heterocycloalkyl ring which can be substituted or unsubstituted. Preferred aminoethers include bis[2-(N,N-dialkylamino)alkyl]ethers characterized by the (N,N-dialkylamino)alkyl]ethers characterized by the formula $R_1R_2NR_3OR_3NR_2R_1$ wherein $R_1$ is a methyl or ethyl group, $R_2$ is a methyl or ethyl group, and $R_3$ is a bivalent alkylene group having from 2 to 4 carbons. Other preferred aminoethers are characterized by the formulae $R_1R_2NR_3OR_4$ or $R_1R_2NR_3OR_5$ wherein $R_1$, $R_2$, $R_3$, $R_4$ and $R_5$ are as defined above. Illustrative aminoethers prepared by the processes of this invention include, for example, bis[2-(N,N-dimethylamino)ethyl]ether, bis[2-(N,N-dimethylamino)-1-methylethyl]ether, bis[3-(N,N-dimethylamino)propyl]ether, bis[2-(N,N-diethylamino)ethyl]ether, bis[2-(N,N-diethylamino-1-methylethyl]ether, bis[2-(N,N-diethylamino)propyl]ether, 2,2-dimorpholinodiethylether, (2-dimethylaminoethyl-3-dimethylaminopropyl)ether, 4-(2-methoxyethyl)morpholine, N-methylmorpholine, N-ethylmorpholine and the like. The preferred bis[2-(N,N-dialkylamino)alkyl]ether is bis[2-(N,N-dimethylamino)ethyl] ether. Illustrative of suitable bis[2-(N,N-dialkylamino)alkyl] ethers which can be prepared by the processes of this invention are described in U.S. Pat. Nos. 3,330,782, 3,400,157, 3,426,072, 3,480,675, 3,957,875, 4,177,212 and 4,247,482, the disclosures of which are incorporated herein by reference.

For instance, in this embodiment of the invention an aminoether is produced by a process comprising the steps of:

i) producing a carboxylated aminoether, such as a di-(tertiary aminoalkyl) carbonate, by a process comprising the step of:

reacting a tertiary alkanolamine with methyl alkyl carbonate in the presence of a transesterification catalyst (such as is described above) to form tertiary aminoalkyl alkyl carbonate and methanol, wherein some of the tertiary alkanolamine reacts with the tertiary aminoalkyl alkyl carbonate to form carboxylated aminoether and alkyl alcohol, under conditions such that the methanol and alkyl alcohol are removed continuously by distillation so that the reactions proceed toward formation of carboxylated aminoether; and ii) contacting the carboxylated aminoether produced in step i) with a metal oxide catalyst under conditions effective to produce the aminoether.

The metal oxide catalyst is selected from the group consisting of one or more oxides of magnesium, aluminum, calcium, strontium, gallium, beryllium, barium, scandium, yttrium, lanthanum, cerium, gadolinium, terbium, dysprosium, holmium, erbium, thulium, lutetium, ytterbium, niobium, tantalum, chromium, molybdenum, tungsten, titanium, zirconium, hafnium, vanadium, iron, cobalt, nickel, zinc, silver, cadmium, boron, indium, silicon, germanium, tin, lead, arsenic, antimony and bismuth, or mixtures thereof. Preferably, the metal oxide catalyst comprises magnesium oxide and aluminum oxide, such as a magnesium:aluminum mixed metal oxide.

For instance, an aminoether such as bis[2-(N,N-dimethylamino)ethyl]ether may be produced by a process comprising the steps of:

i) producing bis[2-(N,N-dimethylamino)ethyl]carbonate by a process comprising the step of:

reacting 2-(N,N-dimethylamino)ethanol with methyl isopropyl carbonate in the presence of a transesterification catalyst (preferably potassium carbonate) to form isopropyl 2-dimethylaminoethyl carbonate and methanol, wherein the 2-(N,N-dimethylamino)ethanol reacts with the isopropyl 2-dimethylaminoethyl carbonate to form bis[2-(N,N-dimethylamino)ethyl] carbonate and isopropanol, under conditions such that the methanol and isopropanol are removed continuously by distillation so that the reactions proceed toward formation of bis [2-(N,N-dimethylamino)ethyl] carbonate; and ii) contacting the bis[2-N,N-dimethylamino)ethyl]carbonate produced in step i) with a metal oxide catalyst under conditions effective to produce the bis[2-(N,N-dimethylamino)ethyl]ether. This latter step, step ii) is sometimes known as the cracking step.

Preferably, the methyl alkyl carbonate (for example, methyl isopropyl carbonate) is formed by reacting dimethyl carbonate with an alcohol (such as isopropanol) in the presence of a transesterification catalyst (preferably sodium methoxide) and an azeotroping agent (preferably cyclohexane) to form a methyl alkyl carbonate (such as methyl isopropyl carbonate) and methanol. It is preferable that this reaction occurs under such conditions that the methyl alkyl carbonate reacts with the alcohol to form di-alkyl carbonate. Similarly, it is preferably that the reaction occurs under such conditions that the tertiary alkanolamine reacts with the di-alkyl carbonate to form more tertiary aminoalkyl alkyl carbonate.

The conditions effective to produce the aminoether, including bis[2-(N,N-dimethylamino)ethyl]ether, as intended in step ii) of this embodiment, are well understood in the art. For instance, such conditions are described in King, U.S. Pat. No. 5,214,142, the entire contents of which are incorporated herein by reference. The preparation of the metal oxide catalyst is accomplished by methods known in the art, such as is described in King, U.S. Pat. No. 5,214,142.

The crude aminoether products produced by the above-described processes can be separated by distillation. Thus, the above-described processes for the manufacture of aminoethers may further include a process for refining the aminoethers produced thereby, which process comprises the step of refining the aminoethers by vacuum distillation. For example, a crude reaction product can be subjected to a distillation-separation at atmospheric or reduced pressure through a packed distillation column.

Figure 2:
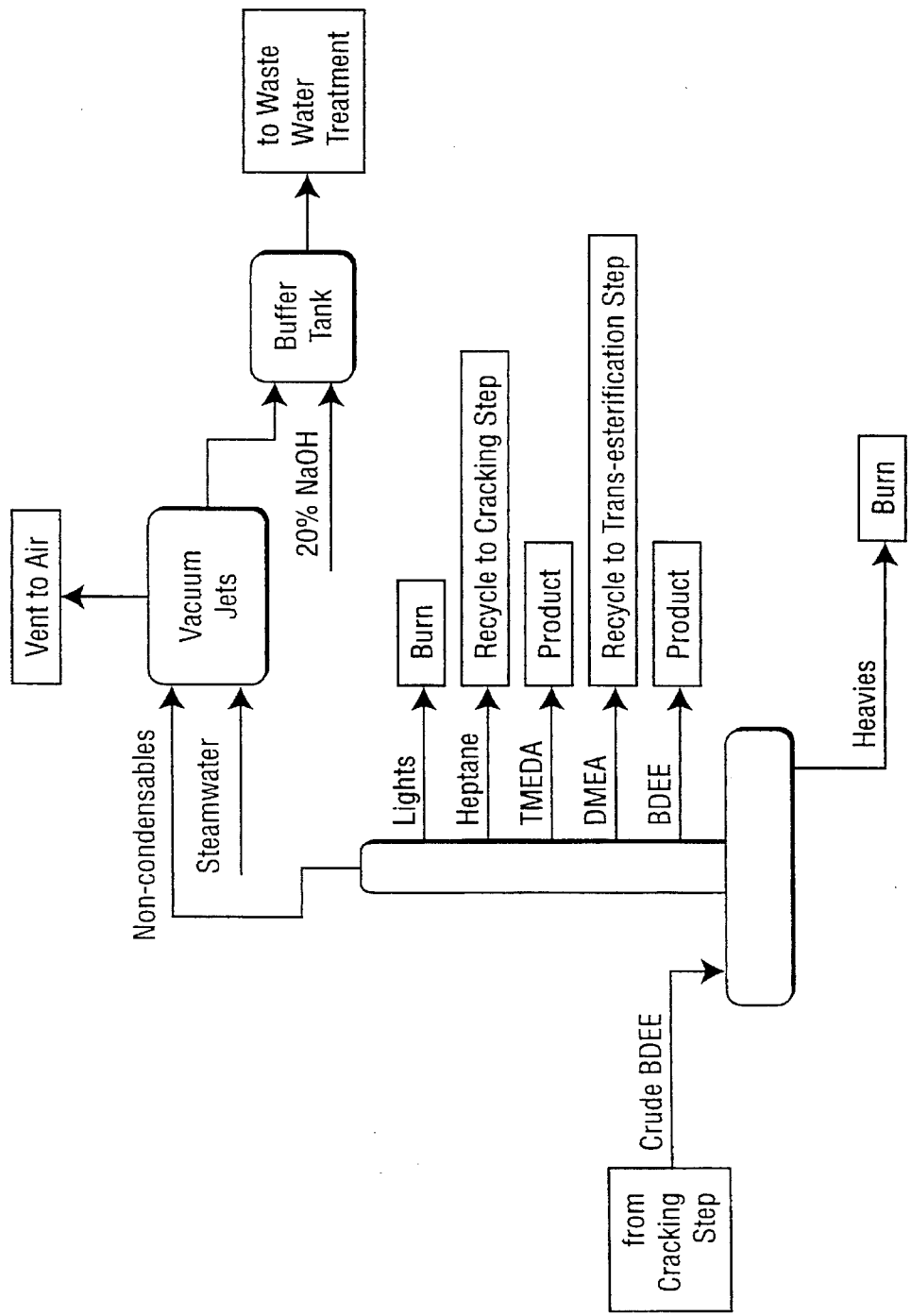
FIG. 2 is a conceptual flow diagram for the refining step.

The conceptual flow diagram for the refining step is shown in FIG. 2. The DDC produced in the transesterification step is converted to BDEE in the cracking step, which is discussed elsewhere. The crude BDEE stream contains BDEE, heptane that was used as a diluent, some unreacted DCC, some DMEA that was either by-product from the cracking or carried through from the transesterification step, by-product TMEDA, and both light and heavy by-products.

The crude BDEE stream is refined in a batch still. Very light materials, referred to as non-condensables, are vented through the vacuum system, where they can be sent to a flare, or scrubbed out with water and, if necessary, treated with caustic soda solution, and sent to a waste water treatment facility. Condensable lights are removed overhead and burned. Heptane is removed overhead and recycled back to the cracking step. TMEDA can be collected as desired. DMEA can be recycled back to the transesterification step. BDEE is removed overhead as the main product. Heavy residue is drained out of the kettle and will be disposed of with other liquid wastes.

In one embodiment of the above-described cracking reaction, DDC is converted to bis(2-dimethylaminoethyl)ether (BDEE) by passing it as a vapor over a specially formulated hydrotalcite catalyst at a temperature of about 315° C. To avoid dew point problems the DDC vapors are mixed with a suitable carrier gas (typically n-heptane) before being directed into the catalyst bed. The exact level of carrier gas required can be determined by the pressure required at the inlet of the reactor to force the mixture through at the rates desired. The DDC will crack over fresh catalyst as shown in the following reaction with an efficiency greater than 65%.

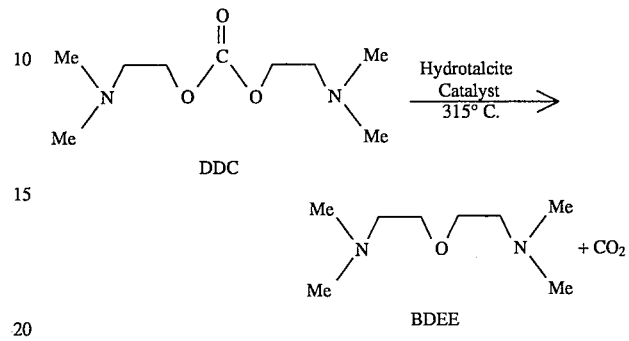

The BDEE (as well as the $CO_2$) will exist as vapor in the reactor. The heat of reaction has been calculated to be slightly exothermic (−1.5 Kcal/gmole) and only a slight temperature rise is expected across the commercial adiabatic cracking reactor.

The most obvious by-product is one due to the transesterification step not being driven to completion with the result that some isopropyl dimethylaminoethyl carbonate (DMEAiPC) is left in the cracker's DDC feed. The DMEAiPC will crack analogously to the reaction for DDC:

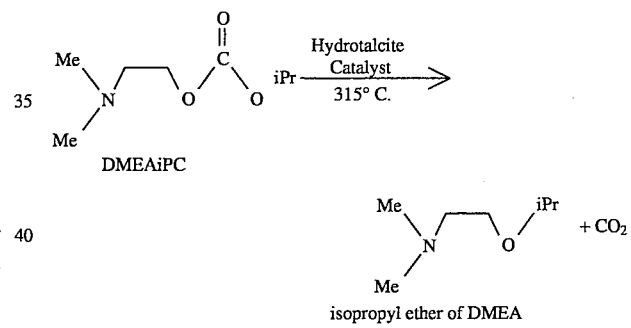

DDC decomposes over the current generation of catalysts in significant amounts to form tetramethylethylenediamine (TMEDA), acetaldehyde, and carbon dioxide as shown in the following reaction:

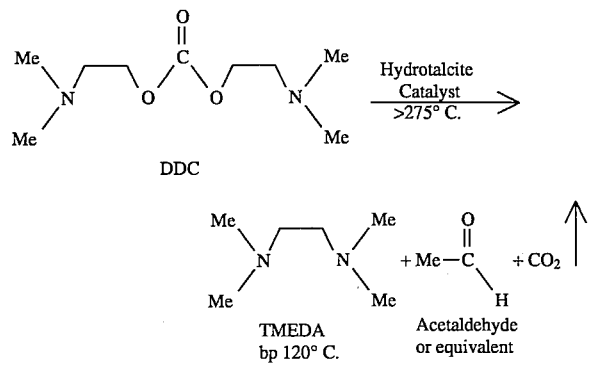

After $CO_2$, TMEDA is the second most plentiful by-product found in the cracker effluent.

Illustratively, the transesterification processes of the invention can be run as batch distillation processes. For instance, the two-step process comprises converting dimethyl carbonate to methyl alkyl carbonate ($MR_eC$) by reaction with the appropriate alcohol ($R_eOH$) in the presence of a catalyst and a suitable azeotroping agent:

$R_eOH$ +

Exchange
Alcohol

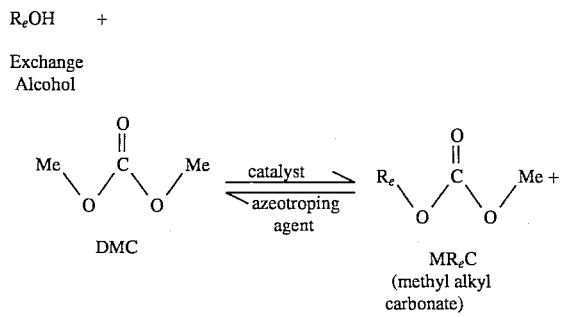

MeOH ↑ (1)

Methanol

Some of the $MR_eC$ can be expected to react further with the Exchange Alcohol to form the di-alkyl carbonate ($DiR_eC$)

$R_eOH$ +

Exchange
Alcohol

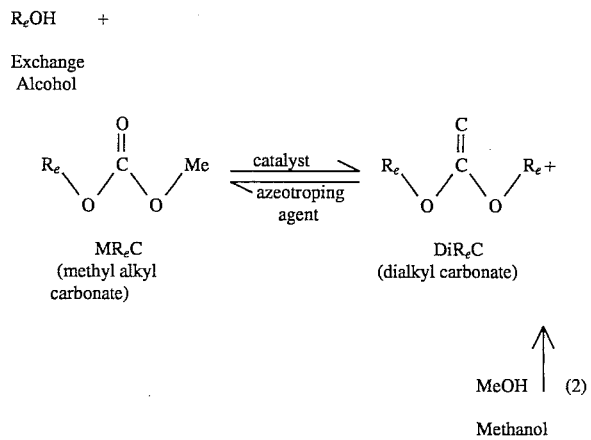

MeOH ↑ (2)

Methanol

But formation of $DiR_eC$ is not detrimental to the eventual objective save for the requirement of larger amounts of Exchange Alcohol. The alcohol can be any alcohol boiling at least 5° C. below the tertiary alkanolamine selected for use and at least 10° C. above the boiling point of methanol, such as in Reaction 3 below.

Preferably, an azeotroping agent is added to the reaction mix to prevent the dimethyl carbonate from coming overhead and to reduce the reaction temperature. The conversion of DMC to $MR_eC$ is stopped when roughly 1–3% of the starting DMC remains. The methanol goes overhead in the distillation column as an azeotrope with the azeotroping agent. In some instances the azeotrope material will phase separate upon cooling into a methanol-rich lower layer. The upper layer will be primarily azeotroping agent with small amounts of methanol and DMC and is suitable for recycling directly to subsequent distillation batches of the process. The lower layer may be suitable for treatment with water to recover azeotroping agent (upper layer) for recycling to subsequent distillation batches. The methanol is treated as a by-product of the process. Methanol contamination of the azeotroping agent for recycle is not a concern since the methanol will eventually work its way out of the system as by-product in future batches.

The required tertiary alkanolamine and catalyst are added at this time to the distillation kettle. The preferred catalyst for this transesterification reaction is potassium carbonate. Potassium carbonate catalyst is preferred for reactions involving tertiary amines because it does not lose activity as readily as sodium methoxide and other alkali alkoxides. Initially the tertiary alkanolamine reacts with $MR_eC$ to yield methanol which is taken overhead with the azeotroping agent and combined with the azeotrope material collected previously so as to recover the azeotroping agent for recycling to subsequent batches.

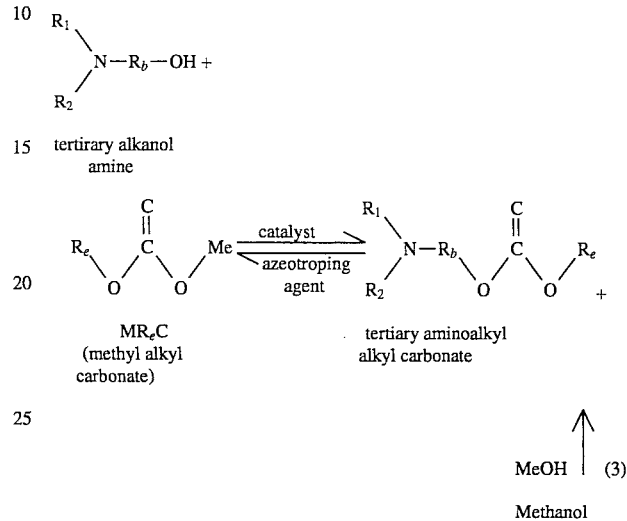

MeOH ↑ (3)

Methanol

When most of the $MR_eC$ has been consumed the tertiary alkanolamine reacts with $DiR_eC$ to form more tertiary aminoalkyl alkyl carbonate and Exchange Alcohol which is distilled overhead first as an azeotrope with the azeotroping agent and then as nearly pure Exchange Alcohol when the azeotroping agent in the kettle is depleted.

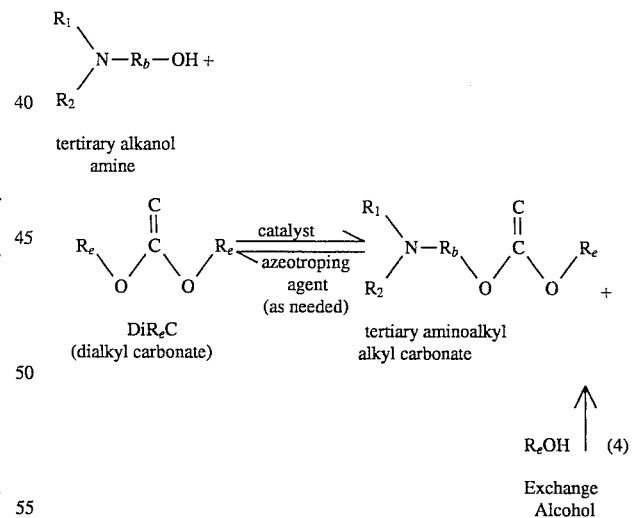

$R_eOH$ ↑ (4)

Exchange
Alcohol

At this time the overhead make can be collected as recycle Exchange Alcohol for use in future batches of the process. Methanol contamination of the Exchange Alcohol recycle is not a concern since the methanol will eventually work its way out of the system as a by-product in future batches. Azeotroping agent contamination of the Exchange Alcohol is also not a concern since the Exchange Alcohol and the azeotroping agent will both be used in the initial charge of a future batch of the process. The relative azeotroping agent and Exchange Alcohol concentrations should be monitored and adjusted as needed to ensure the correct performance of future batches. As the reaction progresses more of the tertiary alkanolamine will react with the accumulating tertiary aminoalkyl alkyl carbonate to yield the desired di-(tertiary aminoalkyl) carbonate.

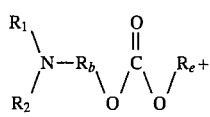

tertiary aminoalkyl alkyl carbonate

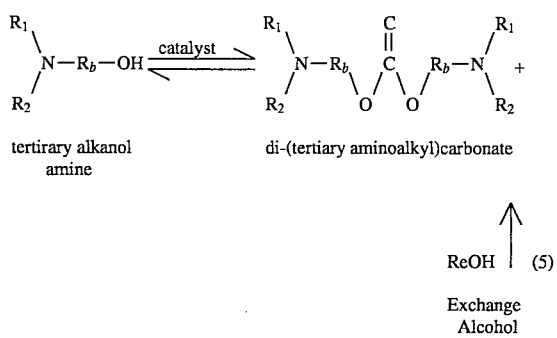

When the concentration of tertiary aminoalkyl alkyl carbonate has fallen to an acceptable level as is dictated by the intended use for the desired di-(tertiary aminoalkyl) carbonate, the Exchange Alcohol removal operation is ended and the excess tertiary alkanolamine removed by distillation. The tertiary alkanolamine taken overhead is of high purity and suitable for use in future batches of the process. The residual desired di-(tertiary aminoalkyl) carbonate is separated from the catalyst solids and then typically distilled overhead at low pressure away from any high boiling by-products or residual catalyst which may be present.

The following Table 1 describes acceptable and preferred ranges of various components of the process.

TABLE 1

| Parameter | Acceptable Range | Preferred Range |
|---|---|---|
| DMC to MR$_c$C conversion: | | |
| starting R$_c$OH/DMC, molar | 1 to 10 | 1.5 to 4 |
| azeotroping agent/DMC, molar | 1.5 to 4 | 2 to 3 |
| reaction pressure, atms. | 0.5 to 5 | 1 to 2 |
| reaction temperature, °C. | determined by pressure | |
| MR$_c$C to di-(tertiary aminoalkyl) carbonate conversion: | | |
| starting tertiary alkanolamine/DMC, molar | 3 to 10 | 3.5 to 5 |
| reaction temperature, °C. | 45 to 135 | 60 to 100 |

Examples of di-tertiary aminoalkyl carbonates that can be manufactured with this process are shown below in Table 2.

TABLE 2

| Final di-tertiary aminoalkyl carbonate | Required alkanolamine for Rxns 3, 4 & 5 |
|---|---|
| bis[2-(N,N-dimethylamino)ethyl]carbonate | 2-(N,N-dimethylamino)ethanol (DMEA) |
| bis[2-(N,N-dimethylamino)-1-methylethyl]carbonate | 2-(N,N-dimethylamino)-1-methylethanol |
| bis[3-(N,N-dimethylamino)propyl]carbonate | 3-(N,N-dimethylamino)propanol |
| bis[2-(N,N-diethylamino)ethyl]carbonate | 2-(N,N-diethylamino)ethanol) |

TABLE 2-continued

| Final di-tertiary aminoalkyl carbonate | Required alkanolamine for Rxns 3, 4 & 5 |
|---|---|
| bis(2-N-morpholinoethyl)carbonate | 4-(2-hydroxyethyl)morpholine |

The di-tertiary aminoalkyl carbonates listed above are shown as examples only and are not intended to limit the application of this invention.

In a preferred embodiment, the invention relates to a batch distillation process for preparing bis[2-(N,N-dimethylamino)ethyl]carbonate (DDC). The process comprises converting dimethyl carbonate to methyl isopropyl carbonate (MiPC) by reaction with isopropanol in the presence of an alkali metal catalyst and cyclohexane azeotroping agent:

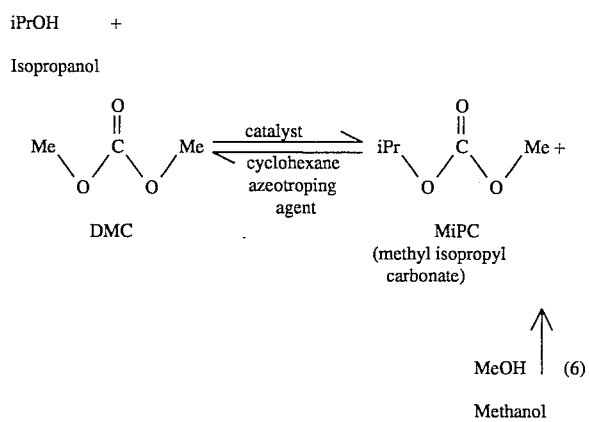

Some of the MiPC can be expected to react further with the isopropanol to form the di-isopropyl carbonate (DiiPC)

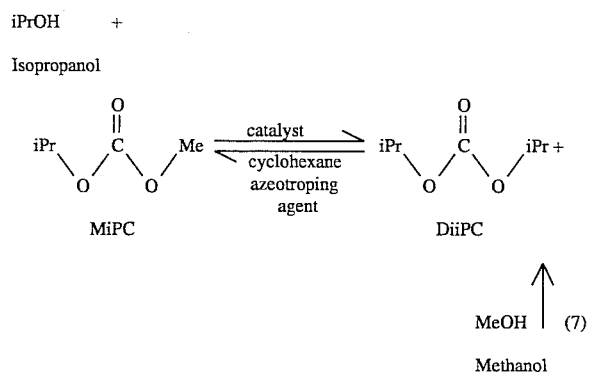

But formation of DiiPC is not detrimental to the eventual objective save for the requirement of larger amounts of isopropanol.

The preferred catalyst used for this reaction is sodium methoxide. Cyclohexane is added to the reaction mix to prevent the dimethyl carbonate from coming overhead and to reduce the reaction temperature. The conversion of DMC to MiPC is stopped when roughly 1–3% of the starting DMC remains. The methanol goes overhead in the distillation column as an azeotrope with cyclohexane which phase separates upon cooling into a methanol-rich lower layer. The upper layer is primarily cyclohexane with small amounts of methanol and DMC and is suitable for recycling directly to subsequent distillation batches of the process. The lower layer can be treated with water to recover cyclohexane for recycling to subsequent distillation batches. The methanol is treated as a by-product of the process. Methanol contamination of the cyclohexane recycle is not a concern since the methanol will eventually work its way out of the system as by-product in future batches.

In a preferred embodiment of this invention DMEA and potassium carbonate catalyst are added at this time to the distillation kettle. The potassium carbonate catalyst is preferred for reactions involving tertiary amines because it does not lose activity as readily as sodium methoxide and other alkali alkoxides. Initially the DMEA reacts with MiPC to yield methanol which is taken overhead with the cyclohexane azeotroping agent and combined with the azeotrope material collected previously so as to recover the cyclohexane for recycling to subsequent batches.

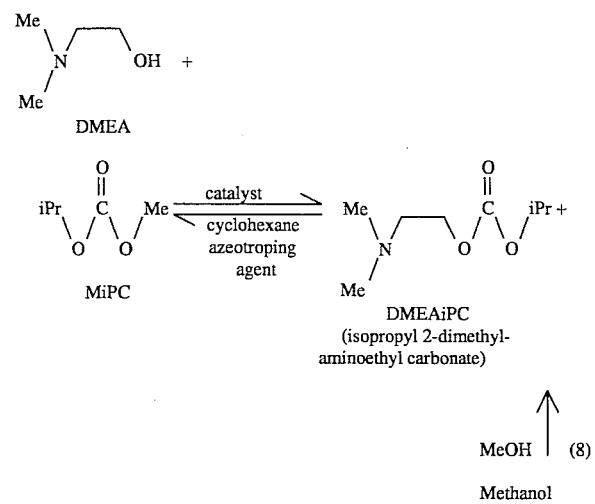

When most of the MiPC has been consumed the DMEA reacts with DiiPC to form more DMEAiPC and isopropanol which is distilled overhead first as an azeotrope with cyclohexane and then as nearly pure isopropanol when the cyclohexane in the kettle is deplete. The reaction seems to run best when the starting DMEA to DiiPC mole ratio is 4 or greater.

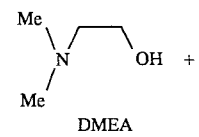

19
-continued

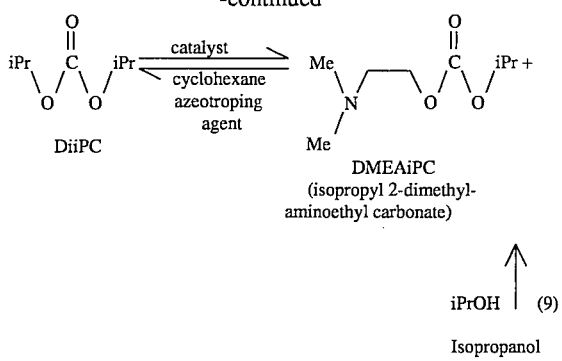

At this time the overhead make is collected as isopropanol for recycling use in future batches of the process. Methanol contamination of the isopropanol recycle is not a concern since the methanol will eventually work its way out of the system as a by-product in future batches. Cyclohexane contamination of the isopropanol is also not a concern since the isopropanol and cyclohexane can both be used in the initial charge of a future batch of the process. The only requirement is that the relative cyclohexane and isopropanol concentrations be monitored and adjusted as needed to ensure the correct performance of future batches. As the reaction progresses more of the DMEA will react with the accumulating DMEAiPC to yield the desired DDC.

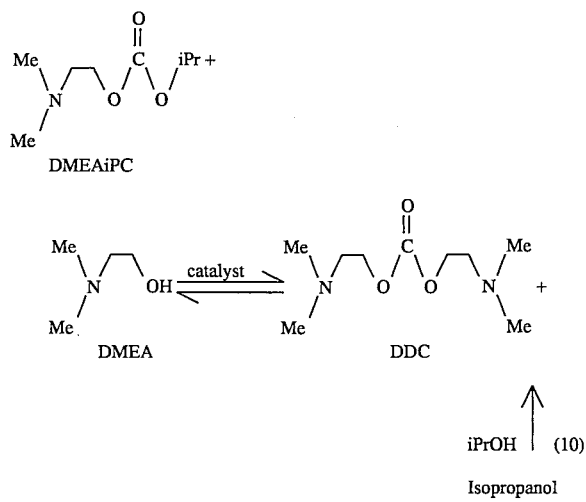

When the concentration of DMEAiPC has fallen to an acceptable level as is dictated by the intended use for the DDC, the isopropanol removal operation is ended and the excess DMEA removed by distillation. The DMEA taken overhead is of high purity and suitable for use in future batches of the process. The residual DDC is separated from the catalyst solids and then typically distilled overhead at low pressure away from any high boiling by-products or residual catalyst which may be present.

By this process DMC can be converted to di-tertiary aminocarbonates in yields of about 90% with purities greater than 99%.

The invention is further described by the following non-limiting examples.

20

EXAMPLES

Example 1

Preparation of bis[2-(N,N-dimethylamino)ethyl]carbonate from dimethyl carbonate via di-n-propyl carbonate (DMC+n-PrOH)

In the kettle of the apparatus shown in FIG. 1 were combined 20 g of TEFLON® (polytetrafluoroethylene) boiling chips, 500.0 g of dimethyl carbonate (DMC), 1000.0 g of cyclohexane, 1001.0 g of n-propanol, and 25.0 g of potassium carbonate in the order indicated. The apparatus was inerted with nitrogen at a pressure of 750 mm Hg and the heating mantle energized. The column reflux ratio was set manually. The column was equilibrated on total reflux for about 45 minutes. The column was then operated with a reflux ratio of 0.3–4:1 while the methanol-cyclohexane azeotrope was distilled overhead carrying with it roughly 1–3% DMC. The overhead liquid phase-separated into a cyclohexane rich upper layer and a lower layer containing about 60% methanol.

When the kettle and middle column temperatures indicated that the concentration of methanol in the kettle was low, the reflux ratio was increased to 10:1. When the overhead temperature reached 74° C. the heating mantle was switched off and the kettle cooled to below 25° C. The overhead make corresponding to the 74° C. overhead temperature did not phase-separate. A gas chromatographic analysis of the kettle contents indicated less than 0.1% methanol, about 0.3% methyl n-propyl carbonate, nil DMC, roughly 25% cyclohexane, roughly 25% n-propanol, and roughly 50% di- n-propyl carbonate.

The charging fitting on the kettle was removed and 1979 g of dimethylethanolamine (DMEA) were added to the kettle mixture. The charging fitting was replaced, the head pressure reduced, and the heating mantle energized. When attempts to operate at a head pressure of 100 mm Hg lead to poor column performance, the head pressure was increased to 200 mm Hg and the column equilibrated at total reflux before taking the remaining cyclohexane overhead.

The overhead pressure was then ramped from 200 mm Hg to 50 mm Hg over about 45 minutes while distilling n-propanol overhead at a reflux ratio of 4:1. The column was operated at 50 mm Hg and a reflux ratio of 4:1 until the head temperature began to climb. The reflux ratio was then increased initially to 10:1 and eventually to 30:1 to minimize DMEA coming overhead. When the concentration of [2-(N, N-dimethylamino)ethyl]n-propyl carbonate dropped below 0.2% in the kettle the head pressure was ramped from 50 mm Hg to 2 mm Hg and all of the unreacted DMEA was distilled overhead at reflux ratios of 2:1 to 0.5:1. The liquid remaining in the kettle was decanted from the solids and transferred to a rotary evaporator where the bis[2-(N,N-dimethylamino)ethyl]carbonate (DDC) was distilled overhead at 0.6 mm Hg using an evaporator bath temperature of 120° C.

The overhead material weighed 875 g and assayed 99.8% DDC by gas chromatographic analysis. The overall material balance was 99.7% and the DDC yield was 77% based on the starting DMC.

Example 2

Preparation of bis[2-(N,N-dimethylamino)ethyl]carbonate from dimethyl carbonate via di-i-propyl carbonate (DMC+i-PrOH)

In the kettle of the apparatus shown in FIG. 1 were combined 20 g of TEFLON® boiling chips, 500.0 g of dimethyl carbonate (DMC), 1000.5 g of cyclohexane, 1000.2 g of isopropanol, and 25.0 g of potassium carbonate ($K_2CO_3$) in the order indicated. The apparatus was inerted with nitrogen at a pressure of 750 mm Hg and the heating mantle energized. The column was equilibrated on total reflux for about 4 hours. It was apparent that the $K_2CO_3$ catalyst was not sufficiently active at these conditions to catalyze the transesterification at a reasonable rate, and consequently 20 ml of sodium methylate solution (5 gm of NaOMe in methanol) was charged to the kettle.

The column was then operated with a minimum reflux ratio of 10:1 while the methanolcyclohexane azeotrope was distilled overhead carrying with it roughly 1–1.5% DMC. During this time the reflux control was set to automatically go to infinite reflux if the column middle temperature exceeded 66° C. The overhead liquid phase-separated into a cyclohexane rich upper layer and a lower layer containing about 55% methanol.

When the kettle and middle column temperatures indicated that the concentration of methanol in the kettle was low, the reflux ratio was increased to 30:1 and an additional 10 ml of sodium methylate solution (2.5 gm of NaOMe in methanol) was charged to the kettle. The overhead make at this point did not phase-separate. The still was operated at this reflux ratio of 30:1 until the concentration of methyl isopropyl carbonate (MiPC) in the kettle dropped below 1%. The still was then operated at a reflux ratio of 5:1 to remove the remaining cyclohexane as cyclohexane-isopropanol azeotrope.

When the overhead temperature reached 81.5° C. the heating mantle was switched off and the kettle cooled to below 25° C. A gas chromatographic analysis of the kettle contents indicated less than 0.1% methanol, about 0.4% methyl isopropyl carbonate, nil DMC, less than 0.4% cyclohexane, roughly 14% isopropanol, and roughly 85% diisopropyl carbonate (DiiPC).

The charging fitting on the kettle was removed and 2110 g of dimethylethanolamine (DMEA) were added to the kettle mixture. The charging fitting was replaced, the head pressure reduced, and the heating mantle energized. The head pressure was reduced to 100 mm Hg and the column equilibrated at total reflux before taking isopropanol overhead at a reflux ratio of 10:1.

When the concentration of [2-(N,N-dimethylamino)ethyl] isopropyl carbonate dropped below 0.1% in the kettle the head pressure was ramped from 100 mm Hg to 2 mm Hg and all of the unreacted DMEA was distilled overhead at a reflux ratio of 2:1. The liquid remaining in the kettle was decanted from the solids and transferred to a rotary evaporator where the bis[2- (N,N-dimethylamino)ethyl]carbonate (DDC) was distilled overhead at 0.5 mm Hg using an evaporator bath temperature of 120° C. The overhead material weighed 952 g and assayed 99.9% DDC by gas chromatographic analysis.

The overall material balance was 99.7% and the DDC yield was 84% based on the starting DMC.

Example 3

Preparation of
bis[2-(N,N-dimethylamino)ethyl]carbonate from
dimethyl carbonate via methyl i-propyl carbonate
(DMC+iPrOH, 2.6% MiPC and DMEA added)

In the kettle of the apparatus shown in FIG. 1 were combined 20 g of TEFLON® boiling chips, 1001.1 g of isopropanol, 999.9 g of cyclohexane, 501.1 g of dimethyl carbonate (DMC), and 31.9 gm of sodium methylate solution (8 gm of NaOMe in methanol) in the order indicated. The apparatus was inerted with nitrogen at a pressure of 750 mm Hg and the heating mantle energized.

After the head temperature indicated distillate had reached the overhead condenser the column was equilibrated on total reflux for about 15 minutes. The column was then operated with a reflux ratio of 10:1 while the methanol-cyclohexane azeotrope was distilled overhead carrying with it roughly 2.7% DMC. The overhead liquid phase-separated into a cyclohexane rich upper layer and a lower layer containing about 48% methanol. When the kettle and middle column temperatures indicated that the concentration of methanol in the kettle was low, the reflux ratio was decreased to 5:1 and cyclohexane-isopropanol azeotrope was distilled overhead. The overhead make at this point did not phase-separate.

When the overhead temperature reached 80° C. the heating mantle was switched off and the kettle cooled to below 25° C. A gas chromatographic analysis of the kettle contents indicated about 0.1 methanol, about 2.6% methyl isopropyl carbonate, nil DMC, less than 1% cyclohexane, roughly 14% isopropanol, and roughly 83% di-isopropyl carbonate (DiiPC).

After removing the charging fitting on the kettle 25.1 gm of potassium carbonate and 1975.6 gm of dimethylethanolamine (DMEA) were added to the kettle mixture. The charging fitting was replaced, the head pressure reduced, and the heating mantle energized. The head pressure was reduced to 200 mm Hg and the column equilibrated at total reflux before taking isopropanol overhead at a reflux ratio of 5:1.

When the kettle temperature reached 84° C. the head pressure in the still was ramped linearly to 100 mm Hg over 45 minutes. Isopropanol was taken overhead for 70 minutes until the head temperature reached 48° C. indicating that most of the isopropanol had been removed from the kettle. The head pressure was then ramped from 100 mm Hg to 2 mm Hg and all of the unreacted DMEA was distilled overhead at a reflux ratios of 2:1. The liquid remaining in the kettle was decanted from the solids and transferred to a rotary evaporator where the bis[2-(N,N-dimethylamino)ethyl]carbonate (DDC) was distilled overhead at 0.6 mm Hg using an evaporator bath temperature of 120° C.

The overhead material weighed 974 g and assayed 99.8% DDC by gas chromatographic analysis. The overall material balance was 99.1% and the DDC yield was 86% based on the starting DMC.

Example 4

Preparation of
bis[2-(N,N-dimethylamino)ethyl]carbonate from
dimethyl carbonate via methyl i-propyl carbonate
(DMC+iPrOH, 3.0% MiPC at DMEA addition)

In the kettle of the apparatus shown in FIG. 1 were combined 20 g of TEFLON® boiling chips, 2000.0 g of isopropanol, 2000.0 g of cyclohexane, 1000.1 g of dimethyl carbonate (DMC), and 63.8 gm of sodium methylate solution (16 gm of NaOMe in methanol) in the order indicated. The apparatus was inerted with nitrogen at a pressure of 740 mm Hg and the heating mantle energized. After the head temperature indicated distillate had reached the overhead condenser the column was equilibrated on total reflux for about 10 minutes. The column was then operated with a reflux ratio of 3:1 while the methanol-cyclohexane azeotrope was distilled overhead carrying with it roughly 3.8% DMC.

During this time the reflux control was set to automatically go to infinite reflux if the column middle temperature exceeded 60° C. The overhead liquid phase- separated into a cyclohexane rich upper layer and a lower layer containing about 55% methanol. When a GC analysis of a kettle sample and the middle column temperatures indicated that the concentration of methanol in the kettle was low, the reflux ratio was fixed at 3:1 and cyclohexane-isopropanol azeotrope was distilled overhead. The overhead make at this point did not phase-separate.

When a GC analysis of a kettle sample indicated that the concentration of MiPC (methyl isopropyl carbonate) had fallen to about 3% in the kettle, the heating mantle was switched off and the kettle cooled to below 47° C. The gas chromatographic analysis of the kettle contents indicated about 0.2% methanol, 3.1% MiPC, nil DMC, about 1% cyclohexane, roughly 16% isopropanol, and roughly 79% di-isopropyl carbonate (DiiPC).

After removing the charging fitting on the kettle 3949.8 gm of dimethylethanolamine (DMEA) and 50.0 gm of potassium carbonate were added to the kettle mixture. The charging fitting was replaced, the head pressure reduced to 200 mm Hg, and the heating mantle energized. The column was equilibrated at total reflux before taking isopropanol overhead at a reflux ratio of 3:1 for about 1 hour before the still was shut down for the night.

The next morning the still was restarted and the isopropanol removal continued. When the kettle temperature reached 85° C. the head pressure in the still was ramped linearly to 100 mm Hg over 20 minutes. Isopropanol was taken overhead for 70 minutes until the head temperature reached 48° C. indicating that most of the isopropanol had been removed from the kettle.

The head pressure was then ramped from 100 mm Hg to 52 mm Hg and unreacted DMEA was distilled overhead at a reflux ratio of 2:1 until the kettle temperature reached 80° C. The still was then shut down and the kettle cooled by lowering the mantle and directing compressed air over the kettle's surface.

The liquid remaining in the kettle weighed 3091.2 g and assayed 65% DDC, 35% DMEA by gas chromatographic analysis. The overall material balance was 99.7% and the DDC yield was 88.7% based on the starting DMC. The carbonate accountability was 97.7%.

Comparative Example 1

Preparation of
bis[2-(N,N-dimethylamino)ethyl]carbonate from
diethyl carbonate (DEC+DMEA)

In the kettle of the apparatus shown in FIG. 1 were combined 40.0 gm of boiling stones, 1500.1 gm of dimethylethanolamine (DMEA), 505.0 gm of diethyl carbonate (DEC), and 20.3 gm of potassium carbonate in the order indicated. The apparatus was inerted with nitrogen at a pressure of 750 mm Hg, the heating mantle energized, and the head pressure reduced to approximately 200 mm Hg over a period of 10 minutes. After the head temperature indicated distillate had reached the overhead condenser the column was equilibrated on total reflux for about 15 minutes. The column was then operated with a reflux ratio of 5:1 while ethanol was distilled overhead carrying with it roughly 4% DEC and 1% DMEA. The overhead temperature during this part of the distillation was 48°–49° C. After approximately 380 gm had been distilled overhead the head temperature rapidly climbed to 74° C. indicating that most of the ethanol had been removed.

The heating mantle was de-energized and the head pressure reduced from 200 to 20 mm Hg over about 30 minutes. After stabilizing the pressure at 20 mm Hg for 5 minutes the mantle was re-energized. Within 10 minutes the head temperature reached 41° C. and DMEA was then taken overhead at a reflux ratio of 2:1 for the next 50 minutes. The overhead temperature was 45°–48° C. during most of this period.

When the overhead temperature reached 52° C. (corresponding to a kettle temperature of 118° C.) the reflux ratio was increased to 5:1. After 35 minutes at these conditions the kettle temperature had risen to 137° C. (with an overhead temperature of 113° C.) and the distillation was terminated.

A gas chromatographic analysis of the crude DDC in the kettle at this point indicates 0.3% DMEA, 99% DDC, and 0.04% ethyl [2-(N,N- dimethylamino)ethyl]carbonate (EDC), the balance being unidentified by-products. A portion of this crude DDC was decanted from the solids and transferred to a rotary evaporator where the bis[2-(N,N-dimethylamino)ethyl]carbonate (DDC) was distilled overhead at a pressure of less than 1 mm Hg using an evaporator bath temperature of 111° C.

The overhead material assayed 99.2% DDC by gas chromatographic analysis and amounted to 99.4% of the crude DDC charged to the rotary evaporator. The residual material from the rotary evaporator indicated a non-volatiles content of 0.42% in the crude DDC. The overall material balance was 98.8% and the DDC yield was 90.5% based on the starting DEC. The carbonate accountability was 94%.

Comparative Example 2

Preparation of
bis[2-(N,N-dimethylamino)ethyl]carbonate directly
from dimethyl carbonate (DMC+DMEA)

In the kettle of the apparatus shown in FIG. 1 were combined 20 g of TEFLON® boiling chips, 1000.2 g of cyclohexane, 501.0 g of dimethyl carbonate (DMC), 1976.0 gm of dimethylethanolamine (DMEA), and 25.1 gm of potassium carbonate in the order indicated. The apparatus was inerted with nitrogen at a pressure of 745 mm Hg and the heating mantle energized. After the head temperature indicated distillate had reached the overhead condenser the column was equilibrated on total reflux for about 15 minutes.

The column was then operated with a reflux ratio of 10:1 while methanol-cyclohexane azeotrope was distilled overhead carrying with it roughly 2.1% DMC. The overhead liquid phase-separated into a cyclohexane rich upper layer and a lower layer containing about 54% methanol. After approximately 953 gm had been distilled overhead the heating mantle was de-energized and removed from the kettle, the kettle cooled from 104° C. to below 89° C. in about 20 minutes, and the still left in a stand-by condition over the weekend.

A gas chromatographic analysis of the kettle material on the following Monday morning indicated 17% cyclohexane, 0.3% methanol, 0.06% DMC, 58% DMEA, 19% DDC, and 5% unidentified by-products.

The still was restarted a day later at a head pressure of 745 mm Hg and a reflux ratio of 10:1. When the kettle temperature reached 120° C. the reflux ratio was reduced to 5:1. A head temperature of 67° C. at this point indicates that the overhead was no longer methanol-cyclohexane azeotrope but essentially DMEA-cyclohexane azeotrope. This is consistent with the overhead make not phase-separating.

Material was distilled overhead at these conditions for another 45 minutes, at which time the kettle temperature had risen to 133° C. and the overhead temperature had reached 70° C. The kettle was cooled to below 25° C. and left in a stand-by state for approximately 40 hours.

When operations were resumed the head pressure was reduced to 100 mm at total reflux before taking 268.5 gm overhead at a reflux ratio of 2:1. A gas chromatographic analysis of this overhead material indicated about 50% cyclohexane, 0.3% methanol, 0.3% DMC, 23% DMEA, and 26% of numerous unidentified by-products.

When the kettle temperature reached 89° C. the head pressure in the still was ramped to 4 mm Hg over 35 minutes and 1347 gm of unreacted DMEA (98% purity) was distilled overhead at a reflux ratio of 2:1. The liquid remaining in the kettle weighed 291.2 gm and assayed 0.34% DDC, 3% MDC, 70.5% DMEA, and 26% unidentified by-products by gas chromatographic analysis. The overall material balance was 94.4% and the DDC yield was 0.09% based on the starting DMC.

Comparative Example 3

Preparation of
bis[2-(N,N-dimethylamino)ethyl]carbonate directly
from dimethyl carbonate (DMC+DMEA)

In the kettle of the apparatus shown in FIG. 1 were combined 20 g of TEFLON® boiling chips, 1000.0 g of cyclohexane, 1975.9 gm of dimethylethanolamine (DMEA), 501.0 g of dimethyl carbonate (DMC), and 25.1 gm of potassium carbonate in the order indicated. The apparatus was inerted with nitrogen at a pressure of 745 mm Hg and the heating mantle energized. After the head temperature indicated distillate had reached the overhead condenser the column was equilibrated on total reflux for about 30 minutes. During this time the reflux control was set to operate with a minimum reflux ratio of 2:1 unless the middle temperature exceeded 57° C. in which case the column automatically switched to infinite reflux.

After 35 minutes at these conditions the head pressure was ramped linearly to 500 mm Hg over 30 minutes. For the next 3 hours the reflux control was set to operate with a minimum reflux ratio of 2:1 unless the middle temperature exceeded 48° C. in which case the column automatically switched to infinite reflux. A gas chromatographic analysis of the kettle at this point indicated its composition to be about 16% cyclohexane, 0.2% methanol, nil DMC, 52% DMEA, 1.2% MDC (methyl [2-(N,N-dimethylamino)ethyl] carbonate), 25.5% DDC, and 5% of unidentified by-products.

Material was distilled overhead at these conditions for another 35 minutes at which time the first distillation cut of 875 gm was completed. Upon standing at room temperature this cut phase-separated into a cyclohexane-rich upper layer (384.4 gm) and a methanol-rich lower layer (490.6). The upper phase would be suitable for recycling to subsequent batches in a commercial process while the lower layer would most likely be discarded. Gas chromatography analyses of the upper and lower layers indicated the reconstituted first cut contained on average 5% DMC and 2.2% DMEA.

After collecting cut 1 the reflux ratio was set to 5:1 and the head pressure ramped linearly from 500 mm Hg to 200 mm Hg over a period of about 45 minutes. At this point collection of the second distillation cut (494.9 gm) was ended. This distillation cut also phase-separated, but the bottom phase only amounted to 6.7% of the total cut. Gas chromatography analysis of the kettle indicated about 64% DMEA, 28% DDC, and 8% unidentified by-products.

Following the second cut the reflux ratio was maintained at 5:1 while the head pressure was ramped linearly from 200 mm Hg to 20 mm Hg over about 35 minutes. When the head pressure reached 70 mm Hg the reflux ratio was adjusted to 2:1.

Material was distilled overhead for an additional 40 minutes after the head pressure had stabilized at 20 mm Hg. Distillation cut 3 (1164.6 gm) was terminated at this point and the still was shut down by de-energizing and lowering the heating mantle before cooling the kettle with a stream of compressed air. The third cut did not phase separate and yielded a DMEA purity of 95% by GC analysis.

The liquid remaining in the kettle was decanted from the solids and transferred to a rotary evaporator where the bis[2-(N,N-dimethylamino)ethyl]carbonate (DDC) was distilled overhead at 2 mm Hg using an evaporator bath temperature of 120° C.

The overhead material weighed 714.2 g and assayed 81.3% DDC, 15% DMEA, and 3.4% unidentified by-products by GC analysis. The overall material balance was 97.8% and the DDC yield was 51.6% based on the starting DMC.

Although the invention has been described in some detail by the preceding examples, it is not intended to be limited thereby. As would be understood by someone with ordinary skill in this art, the examples are for illustrative purposes only, and the invention contemplates the generic area as disclosed hereinabove. Various modifications and embodiments of the examples can be made without departing from the spirit and scope of the invention.

The entire contents of all references cited above are incorporated herein by reference.

I claim:

1. A process for producing di-(tertiary aminoalkyl) carbonate comprising the steps of:

i) reacting dimethyl carbonate with an alcohol in the presence of a transesterification catalyst to form a methyl alkyl carbonate and methanol, ii) reacting a tertiary alkanolamine with the methyl alkyl carbonate formed in step i) in the presence of a transesterification catalyst to form tertiary aminoalkyl alkyl carbonate and methanol, wherein some of the tertiary alkanolamine reacts with the tertiary aminoalkyl alkyl carbonate to form di-(tertiary aminoalkyl) carbonate and alkyl alcohol, under conditions such that the methanol and alkyl alcohol are removed continuously by distillation so that the reactions of steps i) and ii) proceed toward formation of di-(tertiary aminoalkyl) carbonate.

2. The process of claim 1, which is carried out in the presence of no more than 0.1 weight percent water.

3. The process of claim 1, wherein step i) occurs under such conditions that some of the methyl alkyl carbonate reacts with the alcohol to form di-alkyl carbonate.

4. The process of claim 1, wherein step ii) occurs under such conditions that some of the tertiary alkanolamine also reacts with the di-alkyl carbonate formed in step i) to form more tertiary aminoalkyl alkyl carbonate.

5. The process of claim 1, wherein the reaction of step i) occurs in the presence of an azeotroping agent.

6. The process of claim 1, wherein the reaction of step ii) occurs in the presence of an azeotroping agent.

7. The process of claim 1, wherein the alcohol has a boiling point at least 5° C. below the boiling point of the tertiary alkanolamine and at least 10° C. above the boiling point of methanol.

8. The process of claim 7, wherein the alcohol is selected from the group consisting of ethanol, i-propanol, n-propanol, n-butanol, sec-butanol, tert-butanol and isomers of amyl alcohol.

9. The process of claim 1, wherein the transesterification catalyst of step i) is selected from the group consisting of sodium alkoxides, potassium alkoxides, lithium alkoxides, cesium alkoxides and potassium carbonate.

10. The process of claim 5, wherein the azeotroping agent is selected from the group consisting of benzene, carbon tetrachloride, chloroform, cyclohexane, n-heptane, mixed isomers of heptane, n-hexane, mixed isomers of hexane, toluene and trichloroethylene.

11. The process of claim 1, wherein the tertiary alkanolamine is selected from the group consisting of 2-(N,N-dimethylamino)ethanol, 2-(N,N-dimethylamino)-1-methylethanol, 3-(N,N-dimethylamino)propanol, 2-(N,N-diethylamino)ethanol and 4-(2-hydroxyethyl)morpholine.

12. The process of claim 1, wherein the transesterification catalyst of step ii) is selected from the group consisting of sodium alkoxides, potassium alkoxides, lithium alkoxides, cesium alkoxides and potassium carbonate.

13. The process of claim 1, wherein the di-tertiary aminoalkyl carbonate is selected from the group consisting of bis[2-(N,N-dimethylamino)ethyl]carbonate, bis[2-(N,N-dimethylamino)-1methylethyl]carbonate, bis[3-N,N-dimethylamino)propyl]carbonate, bis[2-(N,N-diethylamino)ethyl]carbonate and bis(2-N-morpholinoethyl)carbonate.

14. The process of claim 1, wherein the di-(tertiary aminoalkyl) carbonate produced is bis[2-(N,N-dimethylamino)ethyl]carbonate, and the process comprises the steps of:
 i) reacting dimethyl carbonate with isopropanol in the presence of a transesterification catalyst and an azeotroping agent to form a methyl isopropyl carbonate and methanol, under such conditions that the methyl isopropyl carbonate reacts with the isopropanol to form di-isopropyl carbonate,
 ii) reacting 2-(N,N-dimethylamino)ethanol with the methyl isopropyl carbonate formed in step i) in the presence of a transesterification catalyst to form isopropyl 2-dimethylaminoethyl carbonate and methanol, under such conditions that the 2-(N,N-dimethylamino)ethanol also reacts with the di-isopropyl carbonate formed in step i) to form more isopropyl 2-dimethylaminoethyl carbonate,
 wherein the 2-(N,N-dimethylamino)ethanol reacts with the isopropyl 2-dimethylaminoethyl carbonate formed in step ii) to form bis[2-(N,N-dimethylamino)ethyl] carbonate and isopropanol,
 under conditions such that the methanol and isopropanol are removed continuously by distillation so that the reactions of steps i) and ii) proceed toward formation of bis[2-(N,N-dimethylamino)ethyl] carbonate.

15. The process of claim 14, wherein the transesterification catalyst in step i) is sodium methoxide or potassium carbonate.

16. The process of claim 14, wherein the azeotroping agent is cyclohexane.

17. The process of claim 14, wherein the transesterification catalyst in step ii) is potassium carbonate.

18. A process for producing di-(tertiary aminoalkyl) carbonate comprising the step of reacting a tertiary alkanolamine with methyl alkyl carbonate in the presence of a transesterification catalyst to form tertiary aminoalkyl alkyl carbonate and methanol,
 wherein some of the tertiary alkanolamine reacts with the tertiary aminoalkyl alkyl carbonate to form di-(tertiary aminoalkyl) carbonate and alkyl alcohol,
 under conditions such that the methanol and alkyl alcohol are removed on a continuing basis by distillation so that the reactions proceed toward formation of di-(tertiary aminoalkyl) carbonate.

19. The process of claim 18, wherein the methyl alkyl carbonate is selected from the group consisting of methyl n-propyl carbonate, methyl ethyl carbonate, methyl n-butyl carbonate, methyl sec-butyl carbonate, methyl tert-butyl carbonate, and mixed isomers of methyl amyl carbonate.

20. The process of claim 18, wherein the step of reacting a tertiary alkanolamine with methyl alkyl carbonate occurs in the presence of an azeotroping agent.

21. The process of claim 20, wherein the azeotroping agent is selected from the group consisting of benzene, carbon tetrachloride, chloroform, cyclohexane, n-heptane, mixed isomers of heptane, n-hexane, mixed isomers of hexane, toluene and trichloroethylene.

22. The process of claim 18, wherein the tertiary alkanolamine is selected from the group consisting of 2-(N,N-dimethylamino)ethanol, 2-(N,N-dimethylamino)-1-methylethanol, 3-(N,N-dimethylamino)propanol, 2-(N,N-diethylamino)ethanol and 4-(2-hydroxyethyl)morpholine.

23. The process of claim 18, wherein the transesterification catalyst is selected from the group consisting of sodium alkoxides, potassium alkoxides, lithium alkoxides, cesium alkoxides and potassium carbonate.

24. The process of claim 18, wherein the di-tertiary aminoalkyl carbonate is selected from the group consisting of bis[2-(N,N-dimethylamino)ethyl]carbonate, bis[2-(N,N-dimethylamino)-1-methylethyl]carbonate, bis[3-N,N-dimethylamino)propyl]carbonate, bis[2-(N,N-diethylamino)ethyl]carbonate and bis(2-N-morpholinoethyl)carbonate.

25. The process of claim 18, wherein the di-(tertiary aminoalkyl) carbonate is bis[2-(N,N-dimethylamino)ethyl] carbonate, and the process comprises the step of reacting 2-(N,N-dimethylamino)ethanol with methyl isopropyl carbonate in the presence of a transesterification catalyst to form isopropyl 2-dimethylaminoethyl carbonate and methanol,
 wherein some of the 2-(N,N-dimethylamino)ethanol reacts with the isopropyl 2-dimethylaminoethyl carbonate to form bis[2-(N,N-dimethylamino)ethyl] carbonate and isopropanol,
 under conditions such that the methanol and isopropanol are removed continuously by distillation so that the reactions proceed toward formation of bis[2-(N,N-dimethylamino)ethyl] carbonate.

26. The process of claim 25, wherein the transesterification catalyst is potassium carbonate.

27. The process of claim 18 which comprises the additional step of producing an aminoether by contacting the di-(tertiary aminoalkyl) carbonate with a metal oxide catalyst under conditions effective to produce the aminoether.

28. The process of claim 27, wherein the methyl alkyl carbonate is formed by reacting dimethyl carbonate with an alcohol in the presence of a transesterification catalyst and an azeotroping agent to form a methyl alkyl carbonate and methanol.

29. The process of claim 28, which occurs under such conditions that the methyl alkyl carbonate reacts with the alcohol to form di-alkyl carbonate.

30. The process of claim 29, which occurs under such conditions that the tertiary alkanolamine reacts with the di-alkyl carbonate to form more tertiary aminoalkyl alkyl carbonate.

31. The process of claim 27, wherein the aminoether is selected from the group consisting of bis[2-(N,N-dimethylamino)ethyl]ether, 2,2-dimorpholinodiethylether, 4-(2-methoxyethyl)morpholine, (2-dimethylaminoethyl-3-dimethylaminopropyl)ether, N-methylmorpholine and N-ethylmorpholine.

32. The process of claim 25, which further comprises the step of producing bis[2-(N,N-dimethylamino)ethyl]ether by contacting the bis[2-N,N-dimethylamino)ethyl]carbonate with a metal oxide catalyst under conditions effective to produce the bis[2-(N,N-dimethylamino)ethyl]ether.

33. The process of claim 32, wherein the methyl isopropyl carbonate is formed by reacting dimethyl carbonate with isopropanol in the presence of a transesterification catalyst and an azeotroping agent to form a methyl isopropyl carbonate and methanol.

34. The process of claim 33, which occurs under such conditions that the methyl isopropyl carbonate reacts with the isopropanol to form di-isopropyl carbonate.

35. The process of claim 34, which occurs under such conditions that the 2-(N,N-dimethylamino)ethanol reacts with the di-isopropyl carbonate to form isopropyl 2-dimethylaminoethyl carbonate.

36. The process of claim 33, wherein the transesterification catalyst is sodium methoxide.

37. The process of claim 33, wherein the azeotroping agent is cyclohexane.

38. The process of claim 32, wherein the transesterification catalyst is potassium carbonate.

39. The process of claim 32, wherein the metal oxide catalyst is selected from the group consisting of one or more oxides of magnesium, aluminum, calcium, strontium, gallium, beryllium, barium, scandium, yttrium, lanthanum, cerium, gadolinium, terbium, dysprosium, holmium, erbium, thulium, lutetium, ytterbium, niobium, tantalum, chromium, molybdenum, tungsten, titanium, zirconium, hafnium, vanadium, iron, cobalt, nickel, zinc, silver, cadmium, boron, indium, silicon, germanium, tin, lead, arsenic, antimony and bismuth, or mixtures thereof.

40. The process of claim 27, which further comprises the step of refining the aminoether by vacuum distillation.

41. The process of claim 32, which further comprises the step of refining the bis[2-(N,N-dimethylamino)ethyl]ether by vacuum distillation.

42. The process of claim 25 which further comprises the step of producing tetramethylethylenediamine by contacting the bis[2-N,N-dimethylamino)ethyl]carbonate with a metal oxide catalyst under conditions effective to produce the tetramethylethylenediamine.

43. The process of claim 42, wherein the methyl isopropyl carbonate is formed by reacting dimethyl carbonate with isopropanol in the presence of a transesterification catalyst and an azeotroping agent to form a methyl isopropyl carbonate and methanol.

44. The process of claim 6, wherein the azeotroping agent is selected from the group consisting of benzene, carbon tetrachloride, chloroform, cyclohexane, n-heptane, mixed isomers of heptane, n-hexane, mixed isomers of hexane, toluene and trichloroethylene.

* * * * *